US006635692B1

(12) United States Patent
Christie et al.

(10) Patent No.: US 6,635,692 B1
(45) Date of Patent: Oct. 21, 2003

(54) ANTIFOULING POLYMERS

(75) Inventors: Gregor Bruce Yeo Christie, Victoria (AU); Victor Christov, Victoria (AU); Peter Canisius De Nys, New South Wales (AU); Peter Steinberg, New South Wales (AU); Stephen Hodson, Tasmania (AU)

(73) Assignee: Aquaculture CRC Limited, Sydney (AU)

( * ) Notice: Subject to any disclaimer, the term of this patent is extended or adjusted under 35 U.S.C. 154(b) by 0 days.

(21) Appl. No.: 09/445,682

(22) PCT Filed: Jul. 3, 1998

(86) PCT No.: PCT/AU98/00509

§ 371 (c)(1),
(2), (4) Date: Apr. 20, 2001

(87) PCT Pub. No.: WO99/01514

PCT Pub. Date: Jan. 14, 1999

(30) Foreign Application Priority Data

Jul. 4, 1997 (AU) ............................................. PO 7720

(51) Int. Cl.$^7$ .............................. C08K 5/46; C08K 5/15
(52) U.S. Cl. .......................... 523/122; 524/83; 524/111
(58) Field of Search ............................ 523/122; 524/83, 524/111

(56) References Cited

U.S. PATENT DOCUMENTS 4,542,169 A * 9/1985 Costerton ................... 523/121
5,733,613 A * 3/1998 Baeker ...................... 428/34.9

FOREIGN PATENT DOCUMENTS

| EP | 0 147 970 | 7/1985 |
| EP | 0 624 455 | 11/1994 |
| GB | 2277742 | 11/1994 |
| JP | 61145239 | 7/1986 |
| JP | 6256586 | 9/1994 |

* cited by examiner

*Primary Examiner*—Kriellion A. Sanders
(74) *Attorney, Agent, or Firm*—Morgan, Lewis & Bockius LLP

(57) ABSTRACT

A range of extruded polymers incorporating synthetic furanones was manufactured and field tested. Polymers incorporating furanones showed excellent antifouling efficacy and significantly reduced fouling for more than 100 days.

The present inventors have developed polymers that release commercial short-lived biocides or analogues of antifouling compounds isolated from marine algae. A range of polymers incorporating either the commercial isothiazolone Sea-Nine 211™ or a halogenated furanone were effective antifouling treatments in laboratory and field trials. The efficacy of the polymers was dependant on polymer type and the initial concentration of the antifouling compound. The polymers can be extruded as filaments that can be woven into netting or extruded or molding for other applications.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

25 Claims, 9 Drawing Sheets

Sea-nine 211 (Rohm & Hass)

General structure of isothiazolones

General structure of furanones

ANTIFOULING POLYMERS

TECHNICAL FIELD

The present invention is directed to polymer compositions having anti-fouling activity, particularly polymer compositions suitable for marine and fresh water applications.

BACKGROUND ART

Biofouling presents a severe operational problem to aquaculture for example. On fish cages, it restricts water flow through netting which reduces the supply of dissolved oxygen and the removal of excess feed and waste products. In suspended shell-fish culture, a large mass of fouling can compete with the cultured species for food and space, and can overwhelm flotation capacity. Current metal-based antifoulants are undesirable for aquaculture because of possible adverse environmental effects, and consumer concerns that may jeopardise market image. Commercially available, but biodegradable compounds, or naturally occurring antifoulants extracted from marine organisms, may provide an acceptable solution by offering broad spectrum activity, and in the case of natural antifoulants, acting via chemical deterrence rather than toxicity.

Commercialisation of antifouling technology other than paints is still in its infancy, and few field trials are reported in the literature. Although there are many antifouling agents and compositions presently available, the methods typically used to protect an object from fouling in an aqueous environment involve applying some form of protective coating to the surface of the object. Unfortunately, this approach is not suitable for all applications and there is a need for other means of protecting such objects from microbial- or macro-fouling. The present inventors have developed new polymer compositions that contain antifouling agents which have surprising broad-spectrum antifouling characteristics over prolonged periods and at lower concentrations than were previously believed possible.

DISCLOSURE OF INVENTION

In a first general aspect, the present invention consists in a polymer composition having antifouling activity, the composition including a polymer and an organic antifouling agent, and having broad-spectrum antifouling activity for a prolonged period of at least 100 days when substantially immersed in a natural aqueous environment.

The polymer may be any polymer suitable for preparation by extrusion processes known to the art. In particular, polymers containing ethylene-vinyl acetate copolymer (EVA), high-density polyethylene (HDPE), nylon, polypropylene (PP), sodium ionomer, copolymer of ethylene and acrylic acid, or mixtures thereof are suitable. The present invention has been particularly successful using EVA, HDPE polymers, or mixtures thereof. It will be appreciated, however, that other polymers or mixtures may also be suitable to produce antifouling polymer compositions with prolonged and broad-spectrum antifouling activity according to the present invention.

The antifouling agents suitable for the present invention are synthetic antifouling agents belonging to the families of isothiazolones, furanones, or combinations thereof. Examples of suitable isothiazolones and furanones are shown in FIG. 1. Preferably, the isothiazolone antifouling agent is 4,5-dichloro-2-n-octyl-4-isothiazolin-3-one produced and sold by Rohm and Haas under the name Sea-Nine 211™.

Preferably, the furanone antifouling agent is a mixture of the halogenated furanones referred herein as 26/27 or 33/34 where 26 is (1'RS,5E)-3-(1'-Bromoethyl)-4-bromo-5-(bromomethylidene)-2(5H)-furanone;

27 is (1'RS)-3-(1'-Bromoethyl)-5-(dibromomethylidene)-2(5H)-furanone;

33 is (1'RS,5Z)-3-(1'-Bromohexyl)-4-bromo-5-(bromomethylidene)-2(5H)-furanone; and 34 is (1'RS)-3-(1'-Bromohexyl)-5-(dibromomethylidene)-2(5H)-furanone.

In a preferred embodiment of the first aspect of the present invention, the antifouling agents are used at a concentration of about 0.1 to 20%, more preferably from about 1 to 10% (w/w) of polymer composition. It will be appreciated that mixtures of antifouling agents (natural, synthetic, or commercial) may also be used to prepare the polymer compositions according to the present invention.

When using the antifouling agents in the form of isothiazolones or furanones, the present inventors have made the surprising discovery that in use the polymer compositions release amounts of the agent that would not be expected to prevent fouling by organisms. Release studies found that the activity was caused by about ten-fold less of the agent than what has been shown previously. The compositions that had good and persistent activity over a prolonged period released less than 5, and in several cases less than 1 $\mu g/cm^2$/day of the agent. Preferably, these release rates are obtained.

The polymer compositions according to the present invention had significant antifouling activity when tested in marine environments. Preferably the antifouling activity lasts for at least 100 days, more preferably at least 200 days, and even more preferably at least 300 days.

It will be appreciated that the use of the term natural aqueous environment is meant to include oceans, estuaries, lakes, ponds, rivers and aqueous environments where microorganisms (bacteria) or macroorganisms (algae, plants, invertebrates or other taxa) are known to cause fouling, or there is the potential for such fouling.

The polymer compositions according to the present invention can be made by any known means but preferably made by extrusion or molding processes. The distinct advantage of this form of manufacture is that there is the possibility of controlling or manipulating the type of composition produced. For example, fibers may be produced that can be woven into nets, ropes and the like for use in the aquaculture industry. Also, solid structures can be extruded or molded in the form of cages, crates or structural materials for use in aqueous environments. Moreover, the extrusion or molding processes result in efficient blending of the polymer and active ingredient, a factor influencing the low release rates observed by the present inventors.

It will be appreciated that the present invention is not restricted to use in aquaculture applications. Any situation in aqueous conditions where there is a problem of fouling may be applicable. For example, pipes and plumbing equipment may be made from the polymers according to the present invention.

In a preferred form, the present invention consists in a polymer composition having broad-spectrum antifouling activity comprising a polymer selected from the group consisting of ethylene-vinyl acetate copolymer (EVA), high-density polyethylene (HDPE), sodium ionomer, copolymer of ethylene and acrylic acid, and mixtures thereof and one or more organic antifouling agents selected from the group consisting of antifouling agents belonging to the families of isothiazolones, furanones, and combinations thereof, wherein in use the polymer has broad-spectrum antifouling activity for a prolonged period of at least 100 days, preferably at least 200 days, more preferably at least 250 days, and most preferably for at least 300 days when the composition is substantially immersed in a natural aqueous environment, preferably a marine environment.

In a further preferred form, the present invention consists in an antifouling polymer composition comprising a polymer and an isothiazolone or one or more furanone antifouling agents or mixtures thereof, the composition capable of maintaining broad-spectrum antifouling activity in an natural aqueous environment, preferably a marine environment, by releasing less than about 3–5 $\mu g/cm^2$/day of the antifouling agent over a period of greater than 100 days, preferably over 200 days.

The initial release rates of the antifouling agents from the polymers in the first few days of exposure to an aqueous environment were much higher than the values listed above. What was surprising was the finding that after this initial high release rate, there was sustained antifouling activity (greater than 100 days) of the polymers according to the present invention caused by release of very low levels of antifouling agents.

In a second aspect, the present invention consists in the use of the antifouling compositions according to the first aspect of the present invention in the preparation of extruded or molded articles having sustained broad-spectrum antifouling activity for at least 100 days when substantially immersed in a natural aqueous environment.

In a third aspect, the present invention consists in the use of an isothiazolone or one or more furanone antifouling agents, in the manufacture of an antifouling polymer composition having broad spectrum antifouling activity for at least 100 days when the polymer is substantially immersed in a natural aqueous environment.

In a fourth aspect, the present invention consists in an article made from a composition according to the first aspect of the present invention, the article having broad spectrum antifouling activity for at least 100 days when substantially immersed in a natural aqueous environment.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

In order that the present invention may be more clearly understood, preferred forms will be described with reference to the following examples and the accompanying drawings.

MODES FOR CARRYING OUT THE INVENTION

Figure 1A:
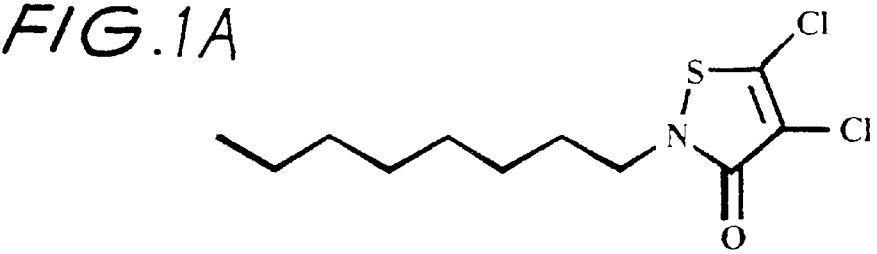
FIG. 1 shows examples of suitable isothiazolones and furanones for the present invention.
In FIG. 1B (isothiazolones), $R_1$, $R_2$ and $R_3$ are either a hydrogen atom, methyl, alkyl, hydroxyl, ether, halogen, sulfur, nitrogen or a combination thereof.
In FIG. 1C (furanones), $R_1$, $R_2$, and $R_3$ are either a hydrogen atom, a hydroxyl group, an alkyl group, an ester group, or a halogenated alkene; or $R_1$ and $R_2$ together are an unsubstituted or a halogenated alkene, $R_4$ is a hydrogen or a halogen atom, and $R_5$ is a hydrogen or an alkyl group.
Figure 1B:
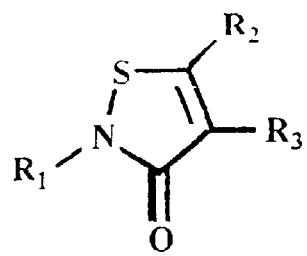
Figure 1C:
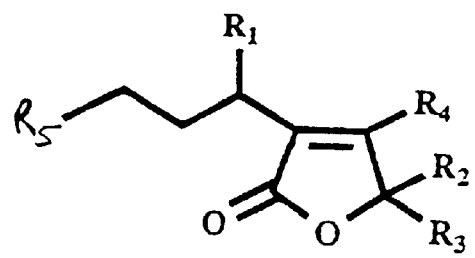

The present inventors have carried out laboratory and field trials of extruded polymers (plastics) that incorporate antifouling compounds. These polymers can be extruded as filaments for fish-cage netting and as rigid mesh for shellfish containment. Antifouling efficacy was evaluated for polymers incorporating either an algal extract, an analog of a compound that occurs in one of these extracts, or one of four commercially-available organic biocides. Antifoulant release from different types of polymer and from polymers with different antifoulant loadings was also investigated. Analysis of micro- and macro-fouling succession clearly demonstrates the potential for polymer-based delivery of antifoulants, and has identified future directions for research into environmentally-acceptable aquaculture antifouling.

MATERIALS AND METHODS

To incorporate commercial biocides, algal extracts or natural product analogues into polymers, the active ingredients were coated onto the polymer beads and compounded as follows:

EXAMPLE I

Single Polymer (HDPE) Incorporating Sea-Nine 211™

The materials were prepared by extruding narrow sheets using a Haake Rheocode 90 system equipped with a laboratory-scale Rheomex TW 100 counter-rotation twin screw extruder fitted with a slit die. The dimensions of the die were: width=15 cm and thickness=1 mm. The Sea-Nine 211™ was premixed with HDPE in the formulation: HDPE: Dried Sea-Nine 211™=95:5.

The screw rotation speed was 50 rpm. The temperature profile along the extruder barrel was set at 160, 170, 180, 170° C. (from feed zone to die).

EXAMPLE II

Polymer Blends (HDPE/EVA) Incorporating Sea-Nine 211™

Step 1:

Sea-Nine 211™ is incorporated into EVA at a loading of 10% using a Haake Rheocord 90 system equipped with a laboratory-scale Rheomex TW 100 counter-rotating twin screw extruder fitted with a rod die (F 2 mm). The Sea-Nine 211™ was premixed with EVA in the formulation: EVA:Sea-Nine 211™=90:10.

The screw speed was 60 rpm. The temperature profile along the extruder barrel was set at 110, 110, 120, 130° C. (from feed zone to die). The extruded materials were granulated for next application.

Step II:

HDPE was blended with the EVA incorporating with Sea-Nine 211™ using a Haake Rheocord 90 system equipped with a laboratory-scale Rheomex TW 100 counter-rotating twin screw extruder fitted with a slit die. The dimensions of the die were: width=15 cm and thickness=1 mm. The EVA incorporating with Sea-Nine 211™ was premixed with HDPE in the formulation: HDPE:EVA incorporating Sea-Nine 211™=90:10. The final Sea-Nine 211™ concentration in polymers is 1%. The screw rotation speed was 50 rpm. The temperature profile along the extruder barrel was set at 160, 170, 180, 170° C. (from feed zone to die).

To minimise the exposure of active ingredients to the harsh conditions of processing, the polymer strips were manufactured in a single step, i.e. pellets of polymer and active compounds were fed into the extruder, compounded and formed into a sheet in one step. Polymers were extruded as strips 400 μm thick by 10 cm wide.

Preparation of algal extracts and metabolites

For the algal extracts, the two species of algae were collected in New South Wales, Australia. The algal tissue was frozen, freeze dried, extracted with dichloromethane and the resulting crude extract reduced in vacuo. Furanones were extracted and purified as per de Nys et al (1993, 1995).

Place of field trials

All field trials were conducted at Huon Aquaculture Company's lease at Hideaway Bay (43° 20' S, 147° 01' E), in the Huon River, Tasmania, Australia. The site is fully marine, except for a 2–5% salinity drop to 1 m depth after high rainfall in winter. Water temperatures range from 11° to 17°. Water movement is dominated by tidal flow and current speed varies from 5 to 20 cm/s.

Polymer-based delivery of antifouling compounds I

Antifouling polymers were produced from one polymer type (Dupont Elvax® 3165SB, ethylene-vinyl acetate) which incorporated either a commercial biocide (Busan 11-M1™, Irgarol 1051™ (2-methyl-4-tert-butylamino-6-cyclopropylamino-s-triazine; Ciba-Geigy), Nopcocide N-96™ (tetrachloroisophthalonitrile; Henkel), or Sea-Nine 211™ (4,5-dichloro-2-n-octyl-4-isothiazolin-3-one; Rohm & Haas), or a crude algal-extract (*Delisea pulchra* or *Laurencia rigida*). All biocides were tested as pure solids without solvent additives. Each antifoulant was incorporated into the polymer at a nominal loading of 1% (of polymer dry weight), except for the *D. pulchra* extract which was included at nominal loadings of 1% and 5%. Subsequent GC-MS analyses revealed that loadings were much lower than this (e.g., roughly 0.1% or less) in this trial.

Laboratory Bioassays

Polymer strips were tested in laboratory bioassays (according to de Nys et al., 1996) to determine inhibition of bacterial growth (*Vibrio fischeri*, *Serratia* sp.), and settlement inhibition of barnacle cyprid larvae (*Balanus amphitrite*), bryozoan larvae (*Bugula neritina*), and settlement and germination of spores of *Ulva lactuca*. Inhibition was compared between treatment dishes (polymer with biocides or extracts incorporated), blank polymer controls (polymer without biocides or extracts incorporated), and untreated dishes (no polymer added). The treatment and polymer control dishes were prepared by fixing a disk of polymer (10 cm$^2$ area) to the base of a petri dish (9 cm$^2$ area). All treatments and controls were tested in triplicate.

Polymers which were ineffective after the initial test (week 0) were discarded. Treatments which were effective, because they either inhibited bacterial growth or larval settlement, were placed in seawater (static) and re-tested at weekly intervals until their activity was not significantly different from the blank polymer control. A new blank polymer control was included in each weekly assay.

Field Trial

Polymer samples were cut into 25 cm strips for field testing, attached randomly within 2 large frames and immersed at 1 m depth. Extruded polymer without antifoulant was used as a control. A total of 59 strips were used, but replication varied between treatments (depending on antifoulant availability). The trial commenced on Sep. 17, 1996, and fouling development was recorded using close-up and wide-angle underwater photography after 25, 25, 60 and 75 days immersion.

To provide samples for scanning electron microscopy (SEM) smaller strips (3×13 cm) were attached to a third frame and fixed underneath one of the larger strip-containing panels. Two strips were removed per treatment after 25, 35 and 75 days immersion. During sampling, a central 1 cm by 8 cm block was excised from each strip and prepared for scanning electron microscopy (Hodson and Burke 1994). Each block was cut into eight 1 cm by 1 cm sections for observation.

Polymer-based delivery of antifouling compounds II

Eight types of polymer (Table 1) were combined with either Sea-Nine 211™ or a combination of synthetic analogs (2/8/1) of a halogenated furanone isolated from *D. pulchra* (2 is (5Z)-3-butyl-4-bromo-5-(bromomethylidene)-2(5H)-furanone; 8 is 3-butyl-5-(dibromomethylidene)-2(5H)-furanone; and 1 is 3-butyl-4-bromo-5-(dibromomethylidene)-2(5H)-furanone). The polymers were chosen to give a range of release rates. A polymer equivalent to that used in trial 1 (Dupont Elvax® 470) was used, but with antifoulants at 1%, 5% and 10% loading. Twenty-five treatments were used in total: 8 controls (each polymer without antifoulant), 10 combinations of Sea-Nine 211™ and 7 combinations of the furanone (Table 2).

TABLE 1

Polymer types evaluated in trial II.

| Manufacturer | Name | Chemical Composition |
| --- | --- | --- |
| Dupont | Elvax ® 470[a] | Ethylene-vinyl acetate co-polymer (EVA)[b] |
| Elf atochem | Evatane ® 1005 VN5 | Ethylene-vinyl acetate co-polymer (EVA)[b] |
| Elf atochem | Evatane ® 1020 VN3 | Ethylene-vinyl acetate co-polymer (EVA)[c] |
| Elf atochem | Evatane ® 28.03 | Ethylene-vinyl acetate co-polymer (EVA)[d] |
| Kemcor | HD 6095 | High-density polyethylene (HDPE) |
| Shell | HET 6100 | Polypropylene (PP) |
| Dupont | Surlyn ® 1707 | Na$^+$ ionomer |
| BASF | Lucalen ® A | Copolymer of ethylene and acrylic acid |

[a]equivalent to Elvax ™ 3165 SB, used in trial I
[b]8% vinyl acetate
[c]18% vinyl acetate
[d]28% vinyl acetate

TABLE 2

Polymer and antifoulant combinations evaluated in trial II. Ten replicates were used for each treatment, except where the number of replicates is specified in brackets.

| Polymer type | Percent antifoulant | Sea-Nine 211 ™ | Halogenated furanones[a] |
|---|---|---|---|
| Dupont Elvax ® 470 | 1% | ✓ | ✓ |
| Dupont Elvax ® 470 | 5% | ✓ | ✓(9) |
| Dupont Elvax ® 470 | 10% | ✓ | ✓ |
| Elf altochem Evatane ® 1005 VN5 | 1% | ✓ (6) | X[b] |
| Elf altochem Evatane ® 1020 VN3 | 1% | ✓ (7) | X |
| Elf altochem Evatane ® 28.03 | 1% | ✓ | X |
| Kemcor HD 6095 | 1% | ✓ | ✓ |
| Shell HET 6100 | 1% | ✓ | ✓ (5) |
| Dupont Surlyn ® 1707 | 1% | ✓ | ✓ |
| BASF Lucalen ® A | 1% | ✓ | ✓ |

[a]The halogenated furanones were not included in all polymers because of limited quantity
[b]X = combination not tested Polymers were cut into 18.5 cm-long strips and attached to sections of 10 cm-long PVC piping. The piping was used to create cylindrical test panels (mounted vertically) as this shape has been found to reduce inconsistencies in fouling distribution, increase rapid colonisation by local fouling species and reduce orientation effects. The panels (n=248) were attached to 6 rows of a 6.0 by 9.0 m polyethylene raft. Rows 1 and 2 were used for release-rate measurement, rows 3, 4 and 5 for photographic records of fouling development, and row 6 (10 panels only) for SEM samples. The experiment was set up as a 1-way block design in rows 1 to 5, with randomised placement of duplicates for each treatment in each row. Not all treatments were fully replicated, however, because of limited quantity of some polymers and of the natural product analog.

The raft was immersed at 1.5 m depth. After 20 days immersion 1 cm by 3 cm samples were cut from each polymer-antifoulant panel in rows 1 and 2, and close-up underwater photographs were taken of all panels in rows 3, 4 and 5. Sampling was repeated at approximately 3 week intervals until all polymers failed to inhibit fouling. Because of severe fouling on most panels, wide-angle photography was used after 125 days. Sampling of rows 1 and 2 was reduced after 47 days because most treatments failed to inhibit fouling. Samples cut from rows 1 and 2 were used to quantify the level of antifoulant remaining (via gas chromatography-mass spectrometry), and this data used for calculation of release rates.

RESULTS
Polymer-based delivery of antifouling compounds I
Laboratory Bioassays

Figure 2:
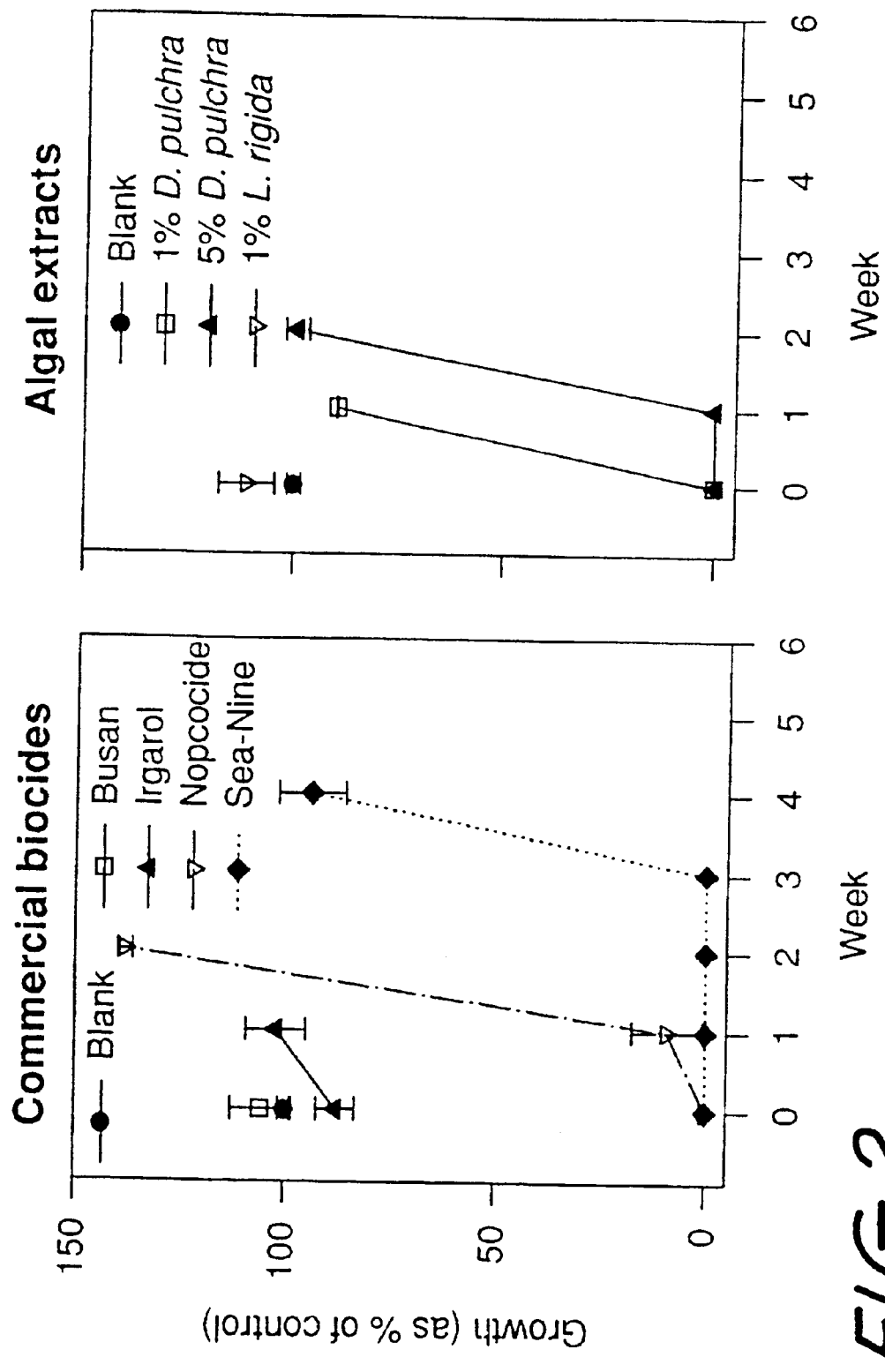
FIG. 2 shows the growth of the marine bacterium *Vibrio fischeri* in culture with polymers incorporating commercial biocides and algal extracts (Data are means±SE, N=3).

Polymers incorporating commercial biocides and extracts significantly inhibited the growth of the marine bacteria *V. fischeri* and Serratia sp. (FIG. 2; $P<0.05$, one-factor ANOVA followed by Tukey's test measured for each assay). Different biocides and extracts had significantly different effects on the growth of both bacteria. The response of both species of bacteria, however, was very similar for most compounds. Sea-Nine 211™ was the most active compound, completely inhibiting the growth of both *V. fischeri* and Serratia sp. for 3 weeks. *D. pulchra* extract (5%) was the next most active compound inhibiting the growth of both species for a period of 2 weeks. Of the other commercial products, Irgarol 1051™ inhibited the growth of Serratia sp. for 2 weeks but was not effective against *V. fischeri*. Similarly Nopcocide N-96™ had differential effects, inhibiting the growth of *V. fischeri* up to 2 weeks, but only inhibiting growth of Serratia sp. for 1 week. The 1% loadings of each algal extract had limited effect on bacterial growth and lost activity after 1 week. Busan 11-M1™ was the least effective compound and was not significantly different from the blank polymer control.

Figure 3:
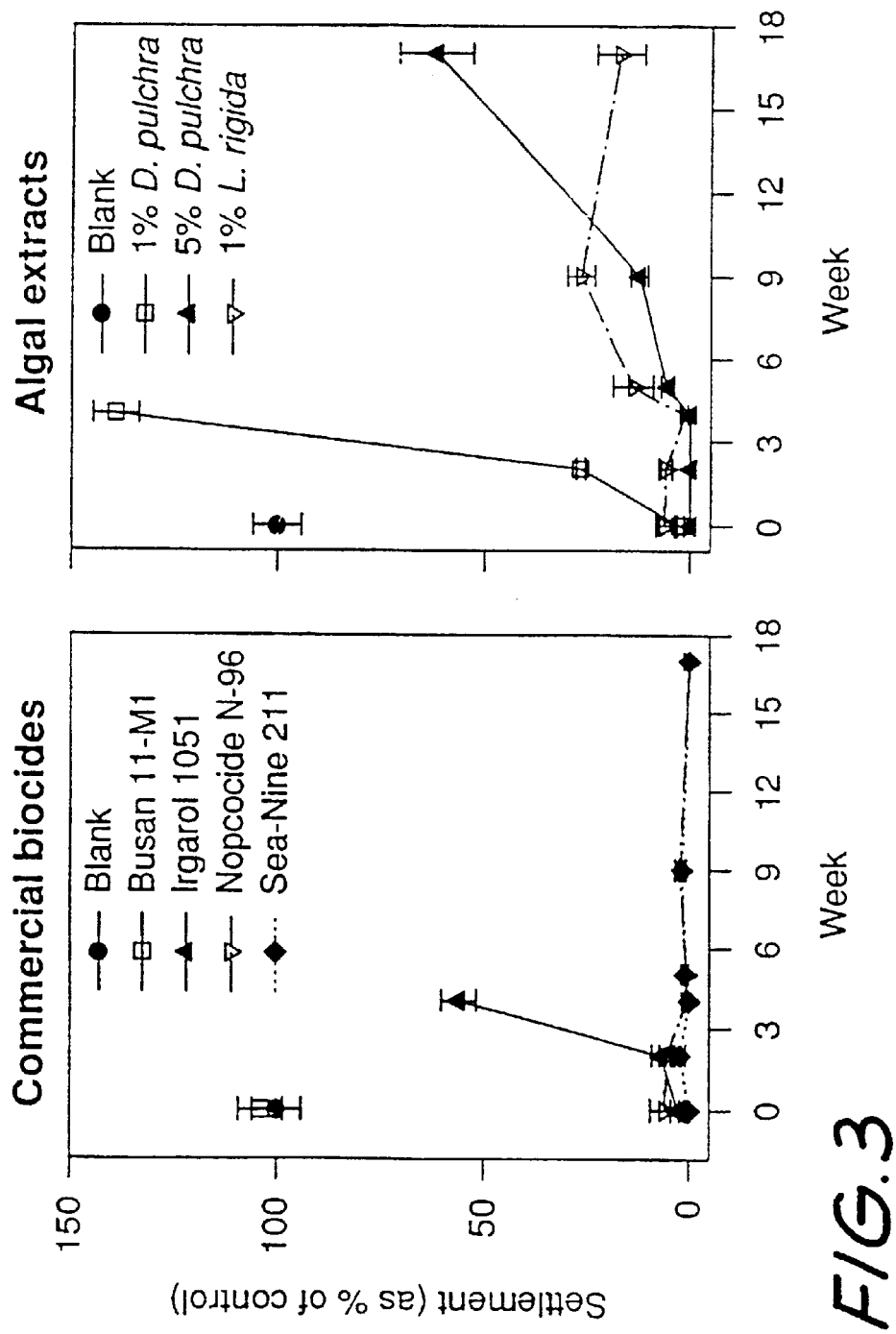
FIG. 3 shows the settlement success of cyprid larvae of *Balanus amphitrite* on polymers incorporating commercial biocides and algal extracts (Data are means±SE, N=3).

The settlement of *B. amphitrite* cyprid larvae was significantly inhibited by the polymers (FIG. 3: $P<0.05$, one-factor ANOVA followed by Tukey's test). Sea-Nine 211™ and Nopcocide N-96™ were the most active compounds completely inhibiting settlement for 17 weeks. The next most effective compound was *L. rigida* extract which after 17 weeks deterred settlement by 80% compared to the control. *D. pulchra* extract (5%) was significantly less effective but remained significantly deterrent, inhibiting settlement by 40% compared to the control. The remaining treatments, Irgarol 1051™ and 1% *D. pulchra* extract, lost activity after 2 weeks. Busan 11-M1™ was the least effective compound and was not significantly different from the blank polymer control.

Figure 4:
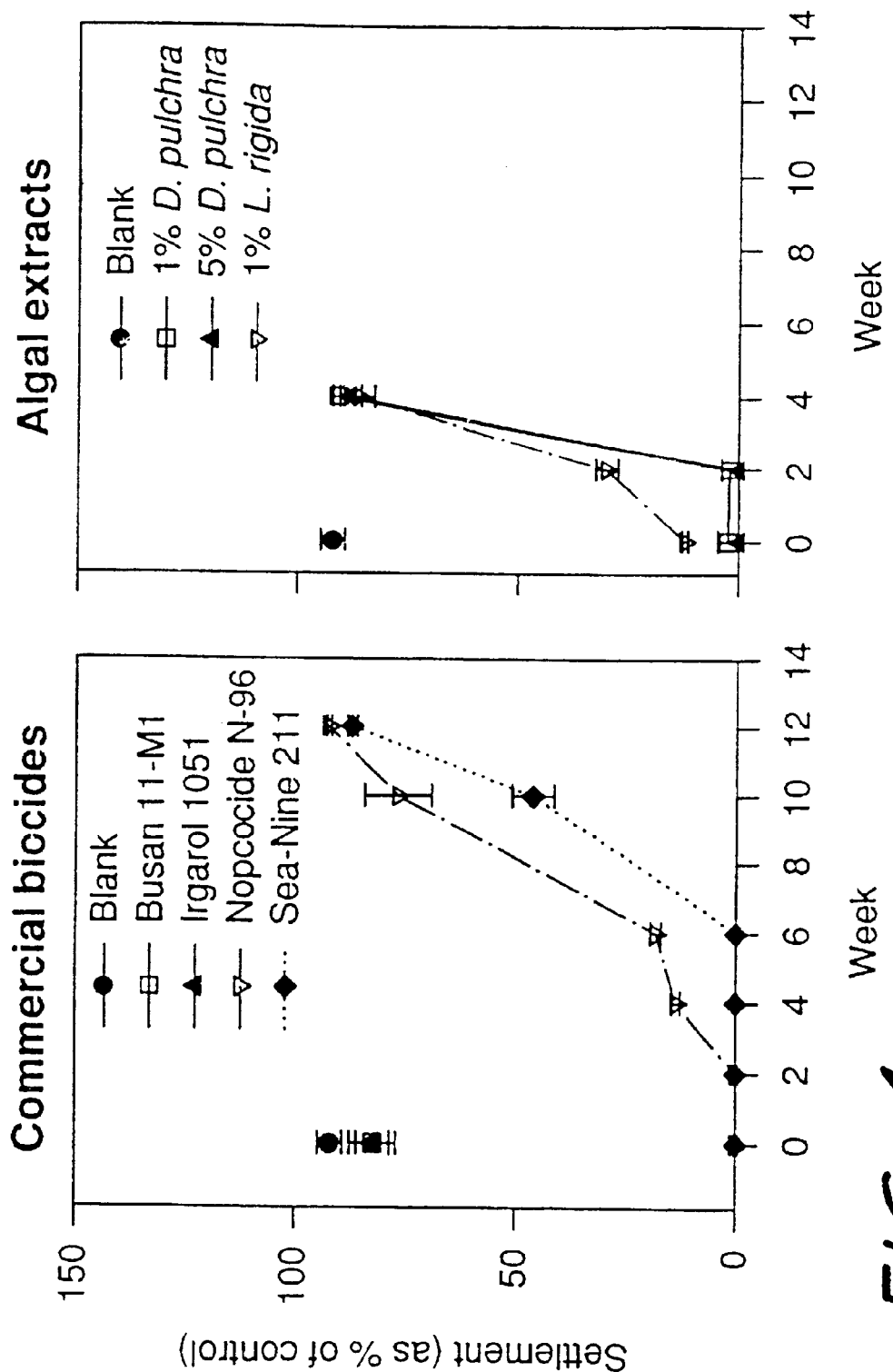
FIG. 4 shows the settlement of larvae of *Bulgla neritina* on polymers incorporating commercial biocides and algal extracts (Data are means±SE, N=3).

The biocides and extracts had significantly different effects on the settlement of *Bugula neritina* larvae (FIG. 4; $P<0.05$, one-factor ANOVA followed by Tukey's test at each time tested). Sea-Nine 211™ was the most effective inhibitory compound, completely inhibiting settlement for 6 weeks and remaining active up to 12 weeks. The next most active compound was Nopcocide N-96™ which significantly deterred settlement for up to 12 weeks. The next group of active compounds, the algal extracts, had a much shorter period of efficacy of 2 weeks. Busan 11-M1™ and Irgarol 1051™ had no significant effect on the settlement of bryozoan larvae.

Field trial

The antifouling effectiveness of both the commercial biocides and algal extracts was demonstrated after 25 days immersion. Polymers with biocides Irgarol 1051™, Nopcocide N-96™ and Sea-Nine 211™ were unfouled and polymer with 5% *D. pulchra* extract had limited fouling. However, the control polymer, polymers containing Busan 1-M1™, 1% *D. pulchra* extract or 1% *L. rigida* extract were heavily fouled. Furthermore, the polymer with *L. rigida* extract had far greater fouling than the control polymer. The dominant fouling at this time was a tube-dwelling diatom (Navicula sp.), a common organism on salmon cages at this time of year. Of the four effective antifouling treatments, Irgarol 1051™ and Sea-Nine 211™ proved superior and still performed well after 60 days immersion. The polymer with 5% *D. pulchra* extract was fouled after 35 days, and the polymer with Nopcocide N-96™ after 60 days.

Polymer observation with SEM clearly demonstrated the same relative performance of the four most effective treatments, but gave an earlier indication of their failure. Polymer with Sea-Nine 211™ performed best, and was only fouled by small colonies of bacteria after 25 days immersion. In comparison, the other two effective biocides displayed a greater level and diversity of macrofouling after 25 days. Polymer containing 5% *D. pulchra* extract was extensively colonised by diatoms within a thick mucilaginous layer. After 35 days polymer with Sea-Nine 211™ was extensively colonised by diatoms, protista and bacteria, but fouling was less severe than on Irgarol 1051™ and Nopcocide N-96™. After 60 days microorganisms were abundant on polymers with Irgarol 1051™ and Sea-Nine 211™.

Polymer-based delivery of antifouling compounds II

Polymers incorporating either the halogenated furanone or Sea-Nine 211™ effectively preventing fouling, although antifouling performance varied between treatments. Within 20 days of immersion all control polymers were covered in tufts of diatoms, whereas all antifouling polymers had either no fouling or a thin diatom film (Table 3). Polymers containing the furanone had good antifouling activity for 50 days, and the nominal 5% and 10% loadings performed better than all other treatments. Six of the polymer types that incorporated Sea-Nine 211™ prevented macrofouling for 260 days immersion. These polymers were frequently fouling by diatom films, but these were poorly adhered and frequently sloughed from the panels. The 5% and 10% loadings of Sea-Nine 211™ had the greatest antifouling effect, and completely prevented the formation of a diatom film for the first 180 days of immersion.

Figure 5:
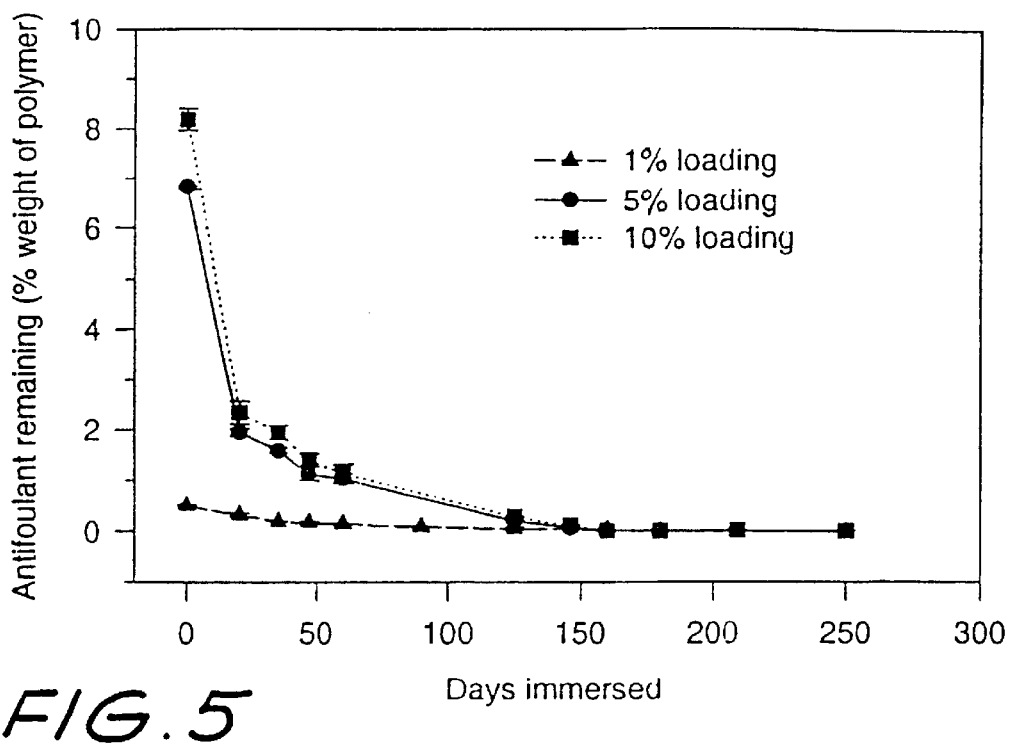
FIG. 5 shows quantities of Sea-Nine 211™ remaining in Dupont Elvax 470 during field exposure. Each point is the mean of 4 samples, bars=standard error.
Figure 6:
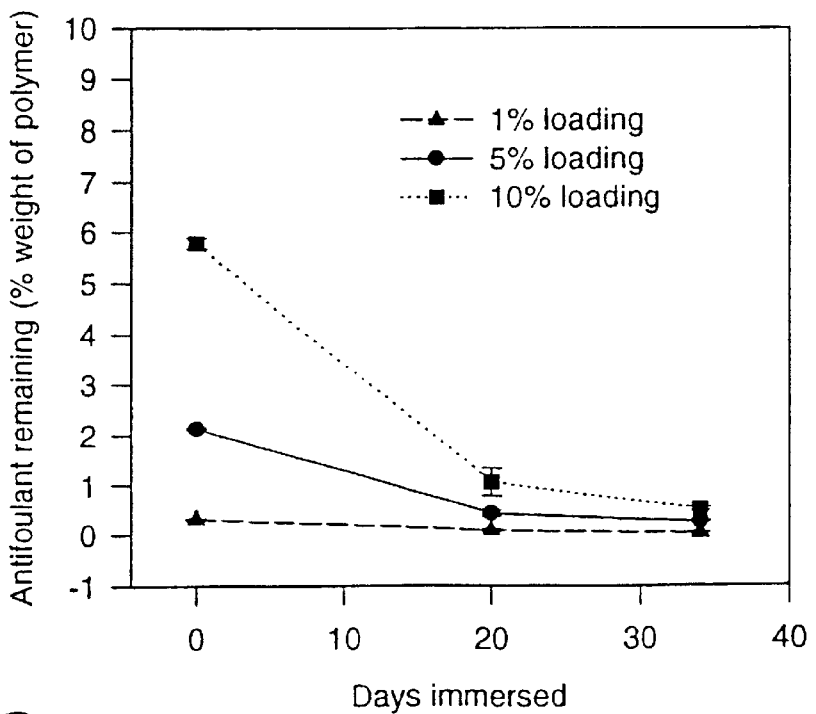
FIG. 6 shows quantities of the halogenated furanone remaining in Dupont Elvax 470 during field exposure. Each point is the mean of 4 samples, bars=standard error.
Figure 7:
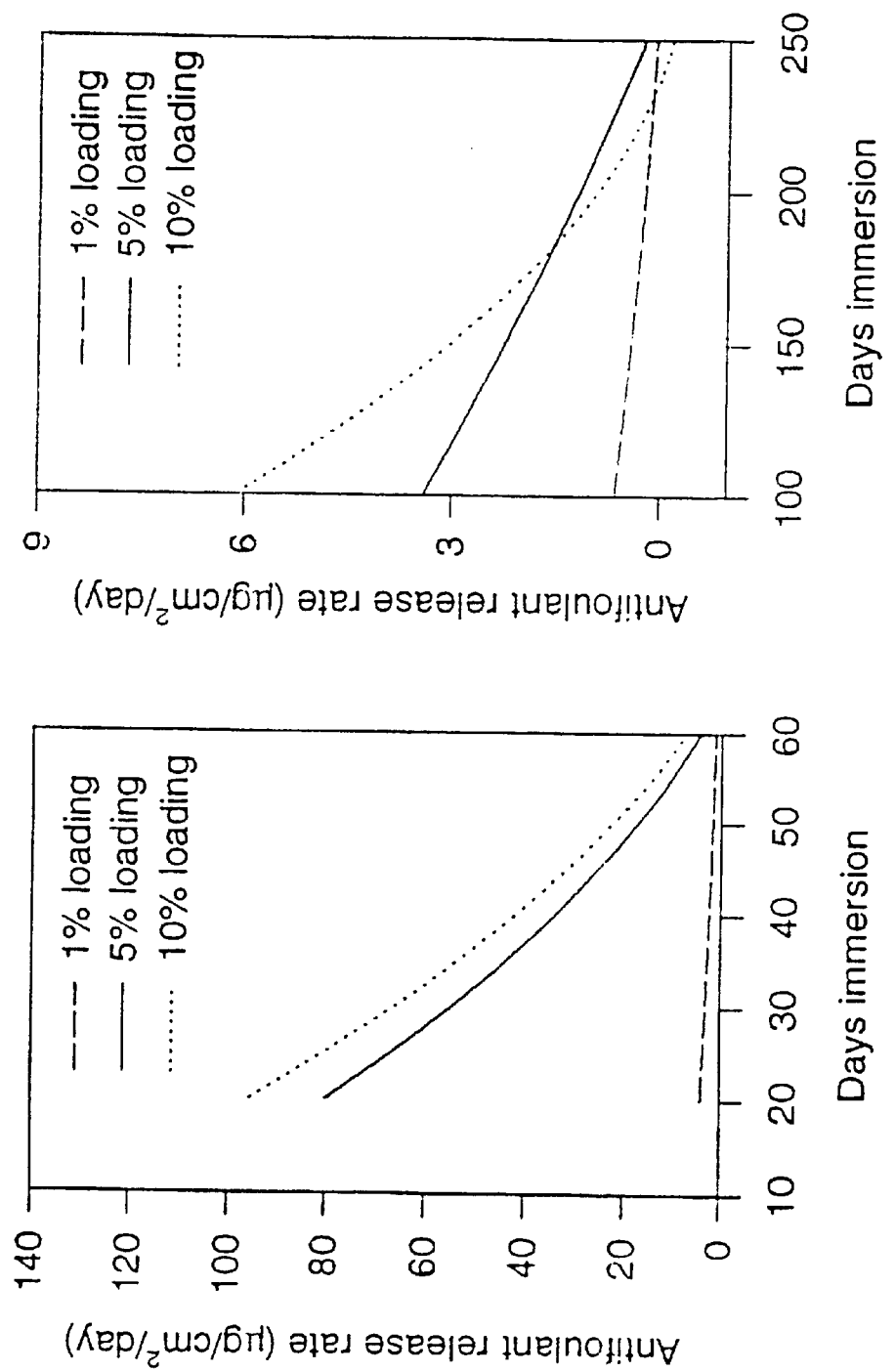
FIG. 7 shows release rate of Sea-Nine 211™ from Dupont Elvax 470 (EVA).

Analysis of the quantity of antifoulant remaining in each polymer during the trial demonstrated varying release rates for each polymer-antifoulant combination. A common trend for all polymer types and concentrations was a high initial release rate during the first 20 days, and then a gradual decline in release (FIGS. 5 and 6). Elvax 3165SB® maintained a relatively constant release rate for Sea-Nine 211™ after 100 days, and demonstrated that only small concentrations of this compound were required for effective antifouling (FIG. 7, Table 4).

Table 4 gives release rates for Sea-Nine 211™ from Elvax 3165SB (=Elvax 470) over 250 days in the second field trial. Release rates were high, but soon decreased to <1 (1% loading) or ~<5 (5% loading) $\mu g/cm^2$/day. In particular both loadings had release rates much lower than 1 $\mu g/cm^2$/day after 160 days in the field trial, but still effectively repelled macrofouling.

TABLE 4

Release rates of Sea-Nine 211 ™ From Elvax 470 ™ in the field. 1% and 5% loading.

| Measurement period | Release Rates ($\mu g/cm^2$/day) | |
| --- | --- | --- |
|  | 1% | 5% |
| 0–20 days | 4.1 | 108.4 |
| 20–47 | 0.9 | 10.8 |
| 47–60 | 0.8 | 3.3 |
| 60–125 | 0.7 | 5.9 |
| 125–160 | 0.2 | 3.4 |
| 160–209 | 0.3 | 0.16 |
| 209–250 | 0.01 | 0.11 |

A range of extrude polymers and antifouling compounds were combined to produce materials with broad-spectrum antifouling efficacy (Table 1 and 2). Seven types of antifouling compound were tested: two algal extracts (from *Delisea pulchra* and *Laurencia rigida*), a halogenated furanone, and four commercial biocides (Busan 11-M1™, Irgarol 1051™, Nopcocide N-96™ and Sea-Nine 211™). Several polymer-compound combinations were highly efficient against fouling in both laboratory and field trials, and are suitable for a range of commercial applications. These include the construction of materials for the aquaculture industry (eg. fish-cage netting, mooring ropes, shellfish trays, rigid mesh panels, buoys and the sides of aquaria) and other applications including piping and cooling-system intake screens.

TABLE 3

Field performance of antifouling polymers which were immersed for 303 days

| | Days immersion | | | | | | | | | | | | |
| --- | --- | --- | --- | --- | --- | --- | --- | --- | --- | --- | --- | --- | --- |
| | 20 | 34 | 47 | 61 | 90 | 110 | 125 | 146 | 160 | 181 | 209 | 259 | 303 |
| Control polymers Sea-Nine 211 ™ | Diatom tufts | | | | | | Macroalgae | | | | | | |
| Elvax 470 (1%) | — | | | | | | Diatom film | | | | | | Macroalgae |
| Elvax 470 (5%) | — | — | — | — | — | — | — | — | — | — | Diatom film | | Macroalgae |
| Elvax 470 (10%) | — | — | — | — | — | — | — | — | — | — | Diatom film | | Macroalgae |
| Evatane 1005 | — | | | | | | Diatom film | | | | | | Macroalgae |
| Evatane 1020 | — | | | | | | Diatom film | | | | | | Macroalgae |
| Evatane 28.03 | — | | | | | | Diatom film | | | | | | Macroalgae |
| Kemcor HD6095 | — | | | | | | Diatom film | | | | | | Macroalgae |
| Shell HET6100 | D.film | | Diatom tufts | | | | | | Macroalgae | | | | |
| Surlyn 1707 | D.film | | Diatom tufts | | | | | | Macroalgae | | | | |
| Lucalen A | — | | | | | | Diatom film | | | | | | Macroalgae |
| Halogenated furanones | | | | | | | | | | | | | |
| Elvax 470 (1%) | D.film | | D.tufts | | | | | | Macroalgae | | | | |
| Elvax 470 (5%) | — | D.film | | D.tufts | | | | | Macroalgae | | | | |
| Elvax 470 (10%) | — | | D.film | | D.tufts | | | | Macroalgae | | | | |
| Kemcor HD6095 | | | Diatom tufts | | | | | | Macroalgae | | | | |
| Shell HET6100 | | | Diatom tufts | | | | | | Macroalgae | | | | |
| Surlyn 1707 | | | Diatom tufts | | | | | | Macroalgae | | | | |
| Lucalen A | D.film | | Diatom tufts | | | | | | Macroalgae | | | | |

— No obvious fouling

Polymers incorporating the commercial isothiazolone Sea-Nine 211™ were highly effective as antifouling materials (Table 3). Sea-Nine 211™ has previously been shown to affect a broad range of fouling taxa, and was more effective than Irgarol 1051™ and Nopcocide N-96™ against growth of *Vibrio fischeri*, settlement of the bryozoan *B. neritina*, and settlement and germination of spores of the alga *Ulva lactuca* (de Nys et al., 1996). Polymers that incorporate this compound are likely to have reduced environmental impact compared with traditional antifouling (eg. tributyl tin coatings), as Sea-Nine 211™ is claimed to rapidly biodegrade (<24 hours) and to not bioaccumulate (Rohm & Haas materials safety data sheets).

Polymers incorporating Sea-Nine 211™ were effective at release rates far lower than recommended for this biocide. The minimum effective release rate (MERR) for Sea-Nine 211™ 10 $\mu g/cm^2/day$ (Takahashi and Mabuchi, 1997). Vasishtha et al. (1995) recommended a MERR of 5–7 $\mu g/cm^2/day$ to prevent fouling by most taxa, with the exception of diatoms (15 $mg/cm^2/day$). In the present study (field trial 2) polymers effectively prevented macrofouling development at release rates lower (in the best case much lower—Table 4) than 1 $\mu g/cm^2/day$ (FIG. 7). At this release rate the polymers did not prevent settlement of a diatom film. However, the release rates (even across a diatom film) were still sufficient to prevent macrofouling.

Such low release rates are ideal for aquaculture, because diatom fouling is not a concern, and the presence of diatoms suggests that release rates were not excessive, ensuring the greatest antifouling lifetime. It is noteworthy that those polymers that prevented development of a diatom film for up to 180 days (Table 3, 5% and 10% loadings of Sea-Nine 211™) were effective at release rates less than 200 nanograms/cm²/day (Tables 3, 4). For aquaculture applications of course, the lower the release rate the better (as long as fouling is still deterred) since impact on the farmed species must be minimized.

The present study demonstrates that the release rate of Sea-Nine 211™ can be controlled by polymer type (Table 1) and by manipulating the initial compound concentration (FIG. 5: Table 4). The migration of an antifouling compound from within a polymer to the water interface is dependent on the diffusivity of the compound within the polymer. The resistance to diffusion will depend on the similarity of the compound and polymer (eg. their hydrophobicity and pH) and interactions between any functional groups of the compound and polymer. However, the antifouling performance of all polymers in the present study is not explained by their relative release rate. The Shell PP™ had the greatest initial concentration of Sea-Nine 211™, and a similar release rate to Elvax 3165™ and Lucalen™, but had poor antifouling efficacy (Table 3). It is probable that this indicates a greater rate of compound dissolution from the polymer into seawater, and therefore a lower concentration at the surface. The present inventors also note that interactions between the polymer, and the active ingredient when it reaches the surface of the polymer, may be very important.

Control of release rates using Polymer Blends

Figure 8:
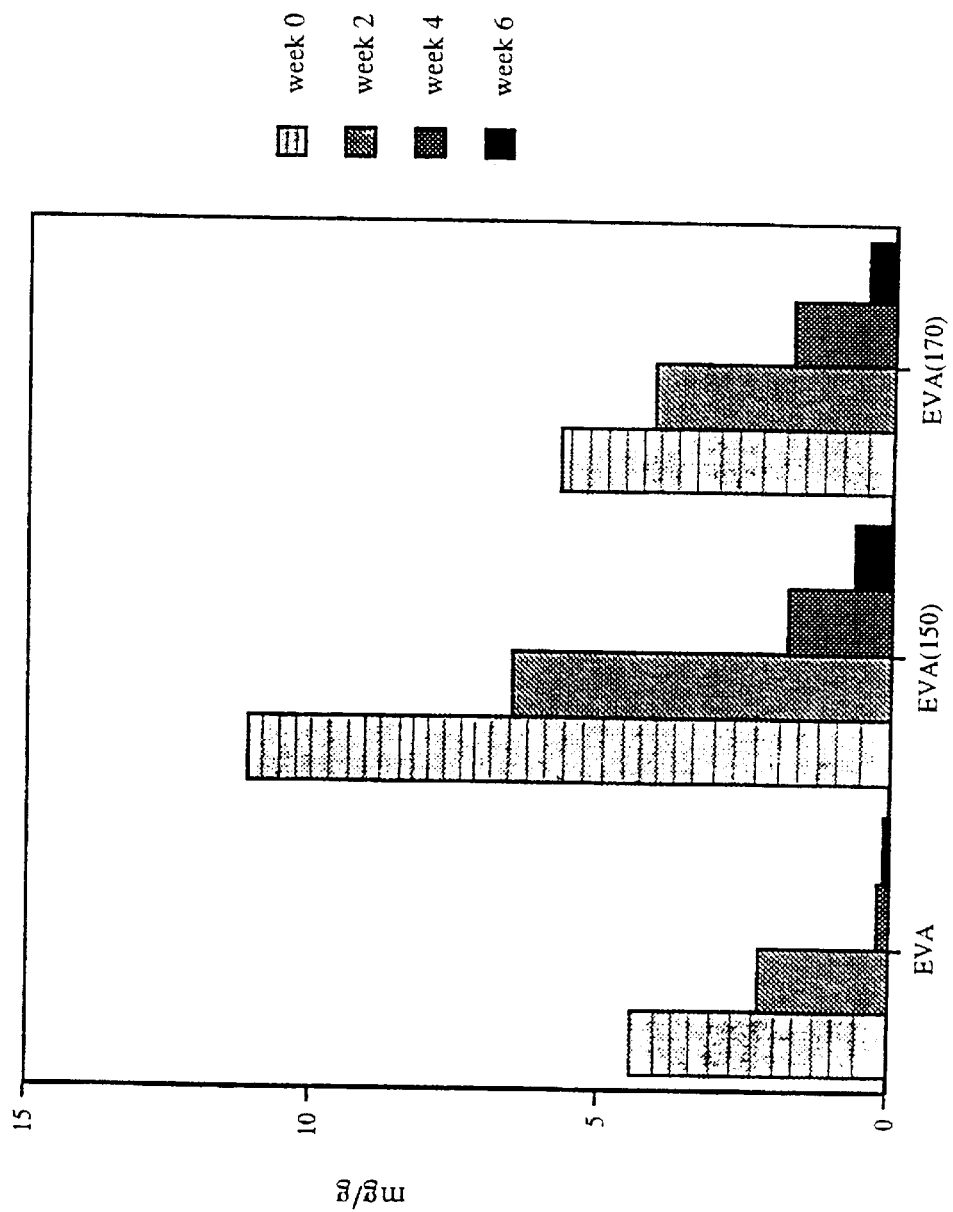
FIG. 8 shows leaching rates for Sea-Nine 211™ from EVA polymers.
Figure 9:
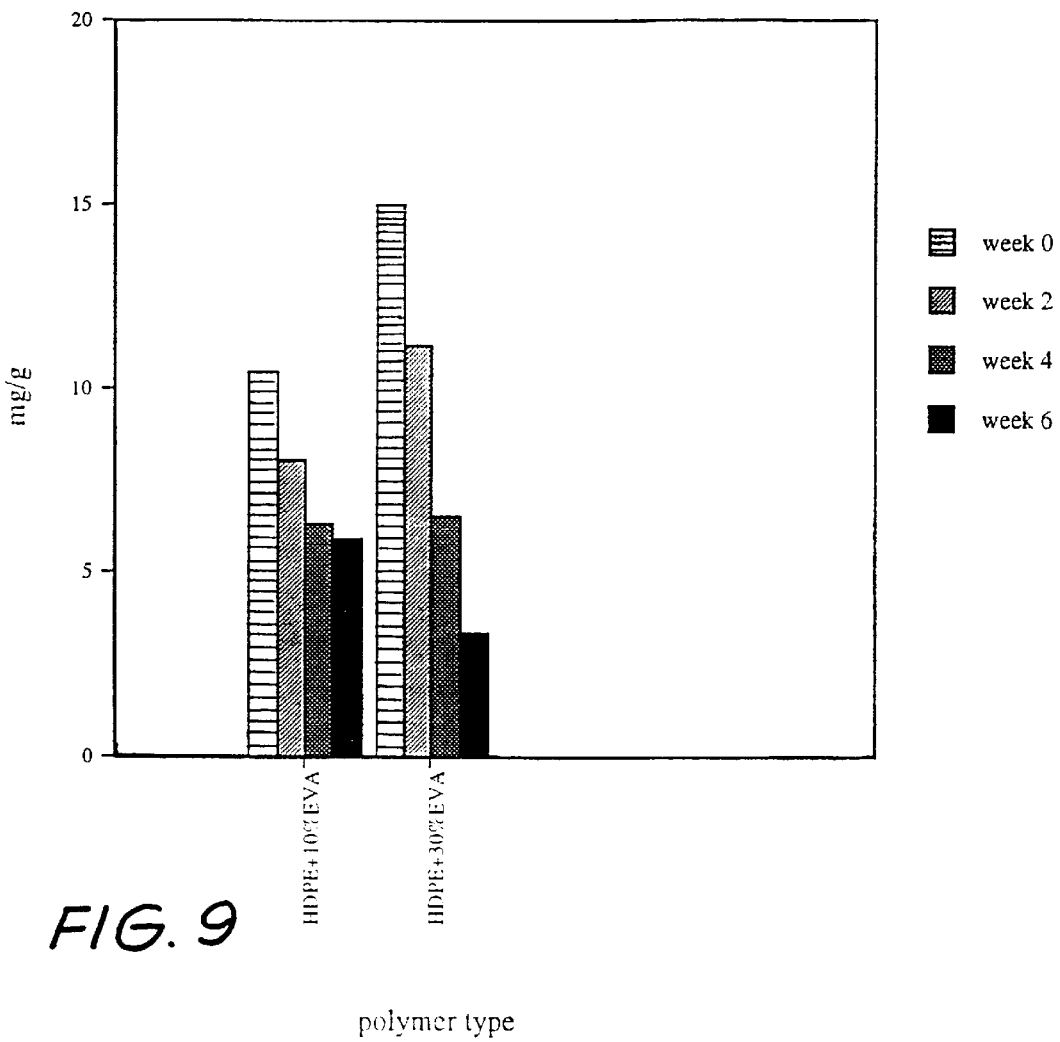
FIG. 9 shows leaching rates for Sea-Nine 211™ from HDPE and EVA blended polymers.
Figure 10:
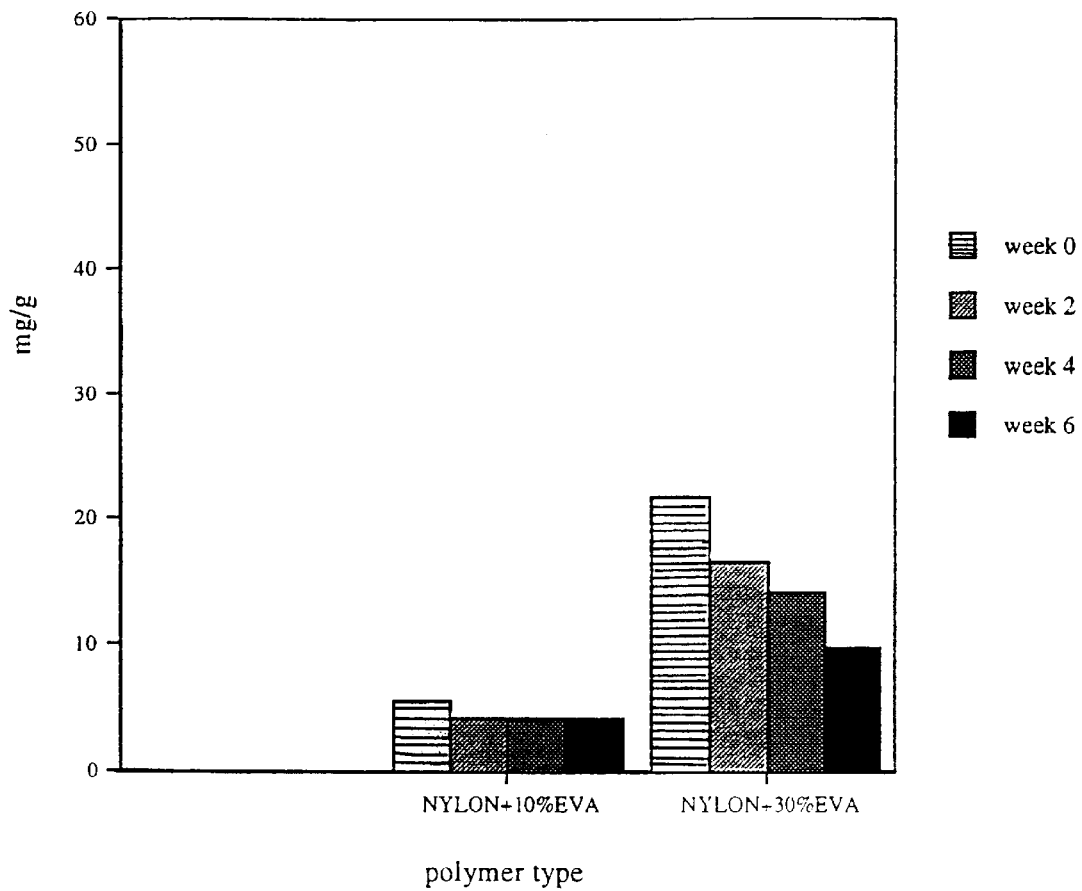
FIG. 10 shows leaching rates for Sea-Nine 211™ from nylon and EVA blended polymers.

From earlier work with Sea-Nine 211™ incorporated into the polymer EVA, it was shown that EVA performed the best in the field trials. However, attempts to significantly extend its active life by incorporating more Sea-Nine 211™ were unsuccessful. This was expected and was due to the zero and first order effects of a matrix device. Adding more active ingredients merely increases the early release rates so that excessive dumping of the component consumes the extra compound added. This can be seen in FIG. 8 where increasing the initial concentration from 4.5 to 6 to 12 mg/g Sea-Nine 211™ resulted in very little improvement in the absolute concentration at week 6, that is 0.2, 0.7. 1 mg/g remaining, respectively. It was discovered that by blending HDPE into the EVA the Sea-Nine 211™ could be retained in the polymer during the initial release period. This is shown in FIG. 9 where with 90% HDPE blended into the EVA (from an initial 11 mg/g loading). 6 mg/g remained in the polymer after 6 weeks compared with 1 mg/g with no HDPE. With reduced amounts of HDPE, the retention effect was reduced. For example, the 70% HDPE only had 3 mg/g (from initial of 15 mg/g) after 6 weeks. The same effect was shown with nylon in FIG. 10 where 90% nylon has 5 mg/g remaining after 6 weeks from an initial 7 mg/g, and 70% nylon had 12 mg/g remaining after 6 weeks from an initial 23 mg/g.

It has been found that the use of other polymers such as HDPE, nylon and the like blended into EVA is an effective way to control the high early release rates of Sea-Nine 211™ when the loading of Sea-Nine 211™ is increased.

Polymers incorporating halogenated furanones were also effective in laboratory and field trials (FIGS. 1, 2, 3, 4: Table 3). Halogenated furanones are active against fouling algae, invertebrates and bacteria (de Nys et al., 1995). Furanones are highly active at low concentrations (10 ng–10 $\mu g/ml$) and effectively inhibit settlement without toxicity. The effective concentrations for furanones are an order of magnitude lower than copper and comparable to, or better than, effective concentrations of Nopcocide N-96™, Irgarol 1051™ and Sea-Nine 211™ in laboratory bioassays.

The difference in antifouling efficacy between Sea-Nine 211™ and furanones appears to be due to the very low initial actual (as opposed to nominal) loadings of furanones, and the apparent need for a greater MERR for these compounds in at least some of the polymers. With regards to loading, the actual loadings of furanones in polymers in the second field trial were much less (between 0.1 and 0.35%) than the target loading of 1%, and thus were much less than the loadings of Sea-Nine 211™ in these trials. With regards to the need of a greater MERR, release rates of furanones from different polymers are shown in Table 5. Elvax 470 and Lucalen A were the most effective in inhibiting fouling, and release rates in these polymers during days 0–20 were $\geq 5 \mu g/cm^2/day$. Lucalen A, and Elvax 470 with 1% loading began to fail after ~35 days, after leaching rates had dropped below 5 $\mu g/cm^2/day$ for 2 weeks (days 20–35). Elvax 470 with a 5% loading of furanones maintained a leaching rate of ~5 $\mu g/cm^2/day$ or higher through 35 days, and inhibiting fouling for this period.

While leaching rates of these furanones thus need to be somewhat higher than for Sea-Nine 211™, the present inventors noted that MERR of 5 $\mu g/cm^2/day$ are very acceptable in both a commercial and environmental sense. They are lower than the recommended MERR for Sea-Nine 211™ (above).

TABLE 5

Release rates of furanones polymers in the field over 35 days

| Polymers | Release Rates ($\mu g/cm^2/day$) | |
|---|---|---|
| | 0–20 days | 20–35 |
| Elvax 470 (5%) | 38.0 | 4.7 |
| Elvax 470 (1%) | 5.0 | 1.4 |
| Lucalen A | 5.8 | 0.4 |
| Kemcor | 1.8 | 0 |
| Shell | 3.0 | 0 |
| Surlyn | 0.1 | 0 |

Incorporation of synthetic furanones into extruded polymers—Antifouling field trial
MATERIALS AND METHODS Nine polymers were extruded for field testing of antifouling efficacy (Table 6). To reduce the high release rates observed with naturally-occurring furanones extracted from *Delisea pulchra* (previous polymer trial) a combination of two synthetic furanone analogs were used: 26/27 and 33/34 where 26 is (1'RS,5E)-3-(1'-Bromoethyl)-4-bromo-5-(bromomethylidene)-2(5H)-furanone; 27 is (1'RS)-3-(1'-Bromoethyl)-5-(dibromomethylidene)-2(5H)-furanone; 33 is (1'RS,5Z)-3-(1'-Bromohexyl)-4-bromo-5-(bromomethylidene)-2(5H)-furanone; and 34 is (1'RS)-3-(1'-Bromohexyl)-5-(dibromomethylidene)-2(5H)-furanone. These were blended into five polymer types. The antifouling efficacy of these polymers was compared against control polymers that did not contain furanones.

Polymers were immersed for field testing in Tasmania, Australia. Testing was conducted at a salmon farm, with panels immersed at 2.0 m depth. For each polymer type there were 3 replicate panels for monitoring of fouling growth (by underwater photography) and 3 replicate panels for release rate analysis. Panels were attached to a 6 m by 2.5 m frame, and each panel was located in a randomly-chosen position. Samples were taken after 2, 4, 7, 10, 13, and 16 weeks to assess release rates and fouling.

TABLE 6

Polymers extruded for field trials with synthetic furanones

| Number | Polymer |
|---|---|
| 1 | Dupont Elvax 470 (ethylene-vinyl acetate. EVA) blank* |
| 2 | Kemcor HDPE 6095 (high-density polyethylene) blank* |
| 3 | Shell PP (polypropylene) blank* |
| 4 | Dupont Elvax 470 (EVA) incorporating 5% furanones 26/27 |
| 5 | Dupont Elvax 470 (EVA) incorporating 5% furanones 33/34 |
| 6 | Kemcor HDPE 6095 incorporating 10% EVA that contained 5% furanones 26/27 |
| 7 | Kemcor HDPE 6095 incorporating 30% EVA that contained 5% furanones 33/34 |
| 8 | Shell PP incorporating 10% EVA that contained 5% furanones 26/27 |
| 9 | Shell PP incorporating 10% EVA that contained 5% furanones 33/34 |

*blank = no furanones added

RESULTS

Control or "blank" polymers (those without furanones) and many of the polymers incorporating furanones were rapidly fouled. After 28 days immersion 100% of the surface area was fouled on most polymers (Table 7). Two of the polymers incorporating furanones, however, were highly inhibitory and had little or no fouling after 28 days (Table 7).

The most efficacious polymer was EVA incorporating furanones 26/27. On this polymer type, only 5% of the surface area was fouled after 91 days. Efficacy was reduced at 112 days, but fouling was still strongly inhibited. This result is better than previous field trials with furanones, in which analogues of naturally-occurring furanones (extracted from algae) were inhibitive for up to 90 days.

TABLE 7

Antifouling performance of polymers incorporating synthetic furanones

| | Percentage of surface area covered by fouling | | | | |
|---|---|---|---|---|---|
| Polymer Type | 14 days | 28 days | 49 days | 91 days | 112 days |
| Blank polymers* | 5 | 100 | 100 | 100 | 100 |
| EVA + 5% furanones 26/27 | 0 | 0 | 5 | 5 | 40 |
| EVA + 5% furanones 33/34 | 0 | 5 | 5 | 25 | 70 |
| HDPE + 10% EVA with 5% furanones 26/27 | 5 | 100 | 100 | 100 | 100 |
| HDPE + 30% EVA with 5% | 5 | 100 | 100 | 100 | 100 |

TABLE 7-continued

Antifouling performance of polymers incorporating synthetic furanones

| | Percentage of surface area covered by fouling | | | | |
|---|---|---|---|---|---|
| Polymer Type | 14 days | 28 days | 49 days | 91 days | 112 days |
| furanones 33/34 | | | | | |
| PP + 10% EVA with 5% furanones 26/27 | 5 | 100 | 100 | 100 | 100 |
| PP + 10% EVA with 5% furanones 33/34 | 5 | 100 | 100 | 100 | 100 |

*All blank polymers had the same antifouling efficacy

REFERENCES de Nys R, Wright A D. Konig G M. Sticher O (1993) New halogenated furanones from the marine red alga *Delisea pulchra* (cf. fimbriata). Tetrahedron 49: 11213–11220.

de Nys R. Steinberg P D. Willemsen P, Dworjanyn S A, Gabelish C L, King R J (1995) Broad spectrum effects of secondary metabolites from the red alga *Delisea pulchra* in antifouling assays. Biofouling 8: 259–271.

de Nys R, Leya T. Maximilien R, Afsar A, Nair P S R, Steinberg P D (1996) The need for standardised broad scale bioassay testing: a case study using the red alga *Laurencia rigida*. Biofouling 10(1–3): 213–224.

Hodson S L. Burke C (1994) Microfouling of salmon-cage netting: a preliminary investigation. Biofouling 8: 93–105.

Dahl B, Blanck H (1996) Toxic effects of the antifouling agent Irgarol 1051 on periphyton communities in coastal water microcosms. Mar Pollut Bull 32: 342–350.

Takahashi K, Mabuchi K (1997) Leaching mechanism of isothiazolone from antifouling paints containing Sea-Nine and clathrate Sea-Nine. U.S. Pacific Rim Workshop on Emerging Nonmetallic Materials for the Marine Environment.

Vasishtha N, Sundberg D C, Rittschof D (1995) Evaluation of release rates and control of biofouling using monolithic coatings containing an isothiazolone. Biofouling 9: 1–16.

What is claimed is:

1. A polymer composition having broad-spectrum antifouling activity comprising a polymer selected from the group consisting of ethylene-vinyl acetate copolymer (EVA), high-density polyethylene (HDPE), sodium ionomer, copolymer of ethylene and acrylic acid, and mixtures thereof and one or more organic antifouling agents selected from the group consisting of antifouling agents belonging to the families of isothiazolones, furanones, and combinations thereof, wherein in use the polymer has broad-spectrum antifouling activity for a prolonged period of at least 100 days when the composition is substantially immersed in a natural aqueous environment.

2. The composition according to claim 1 including at least one of the polymers EVA, HDPE, or mixtures thereof.

3. The composition according to claim 1 wherein the isothiazolone antifouling agent is 4,5-dichloro-2-n-octyl-4-isothiazolin-3-one.

4. The composition according to claim 1 wherein the furanone antifouling agent is selected from a mixture of (1'RS,5E)-3-(1'-Bromoethyl)-4-bromo-5-(bromomethylidene)-2(5H)-furanone and (1'RS)-3-(1'-Bromoethyl)-5-(dibromomethylidene)-2(5H)-furanone; or (1'RS,5Z)-3-(1'-Bromohexyl)-4-bromo-5-(bromomethylidene)-2(5H)-furanone and (1'RS)-3-(1'-Bromohexyl)-5-(bromomethylidene)-2(5H)-furanone.

5. The composition according to claim 1 wherein the antifouling agent is used at a concentration of 0.1 to 20% (w/w) of polymer.

6. The composition according to claim 5 wherein the antifouling agent is used at a concentration of 1 to 10% (w/w) of polymer.

7. The composition according to claim 1 wherein the antifouling activity lasts for at least a 200 days.

8. The composition according to claim 7 wherein the antifouling activity lasts for at least 250 days.

9. The composition according to claim 8 wherein the antifouling activity lasts for at least 300 days.

10. The composition according to claim 1 wherein the broad-spectrum antifouling activity in the natural aqueous environment is achieved by a release-rate about 3–5 $\mu g/cm^2/$ day or less of the antifouling agent over a period of at least 100 days.

11. The composition according to claim 10 wherein the period of release is at least 200 days.

12. The composition according to claim 11 wherein the period of release is at least 300 days.

13. The composition according to claim 1 wherein the composition is extruded or molded into fibers or solid structures in the form of cages, crates or structural materials adapted for use in aqueous environments.

14. An extruded or molded article comprising a composition according to claim 1 wherein the article has sustained broad-spectrum antifouling activity for at least 100 days when substantially immersed in a natural aqueous environment.

15. A method of preventing or minimizing fouling of a natural aqueous environment for a period of at least 100 days, comprising immersing a composition of claim 1 in a natural aqueous environment in an amount effective to provide sustained broad-spectrum anti-fouling activity for a period of at least 100 days.

16. The method of claim 15 wherein the fouling is caused by microorganisms or macroorganisms.

17. A method of preventing or minimizing fouling of a natural aqueous environment for a period of at least 100 days, comprising immersing an extruded or molded article of claim 14 in a natural aqueous environment.

18. The method of claim 17 wherein the extruded or molded article comprises fibers or solid structures in the form of cages, crates or structural materials adapted for use in aqueous environments.

19. The method of claim 17 wherein the fouling is caused by microorganisms or macroorganisms.

20. The article according to claim 14, wherein said article is, or forms a part of, an aquaculture apparatus.

21. The article according to claim 20, wherein the aquaculture apparatus is used in a shellfish culture.

22. The article according to claim 20, wherein the natural aqueous environment is a marine environment.

23. The article according to claim 20, wherein the natural aqueous environment is a fresh water environment.

24. The article according to claim 14, wherein said article is, or forms a part of, plumbing equipment capable of use in a natural aqueous environment.

25. The article according to claim 24, wherein said plumbing equipment is a pipe.

* * * * *